US007848820B2

United States Patent
Abrahamson

(10) Patent No.: US 7,848,820 B2
(45) Date of Patent: Dec. 7, 2010

(54) SYSTEM AND METHOD FOR RADIO COMMUNICATION BETWEEN AN IMPLANTABLE MEDICAL DEVICE AND AN EXTERNAL BASE UNIT

(75) Inventor: Hans Abrahamson, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 701 days.

(21) Appl. No.: 11/909,200

(22) PCT Filed: Apr. 7, 2005

(86) PCT No.: PCT/SE2005/000509

§ 371 (c)(1),
(2), (4) Date: Sep. 20, 2007

(87) PCT Pub. No.: WO2006/107244

PCT Pub. Date: Oct. 12, 2006

(65) Prior Publication Data

US 2009/0264964 A1    Oct. 22, 2009

(51) Int. Cl.
A61N 1/08 (2006.01)
(52) U.S. Cl. .................... 607/60; 607/30; 128/903; 340/539.12

(58) Field of Classification Search ............ 607/30, 607/32, 60; 128/903, 904
See application file for complete search history.

(56) References Cited

U.S. PATENT DOCUMENTS

| 5,350,411 | A | 9/1994 | Ryan et al. |
|---|---|---|---|
| 6,738,670 | B1 | 5/2004 | Almendinger et al. |
| 7,319,903 | B2 * | 1/2008 | Bange et al. .................. 607/60 |
| 2003/0114898 | A1 | 6/2003 | Von Arx et al. |
| 2004/0122488 | A1 | 6/2004 | Mazar |

FOREIGN PATENT DOCUMENTS

WO    WO 03/066163    8/2003

* cited by examiner

Primary Examiner—Carl H Layno
Assistant Examiner—Brian T Gedeon
(74) Attorney, Agent, or Firm—Schiff Hardin LLP

(57) ABSTRACT

In a system and method for radio communication between an implantable medical device (IMD) and an external base unit, respectively including transceivers for communication therebetween, the external base unit, according to a predetermined criterion, sends a sleep message to the IMD transceiver, requesting the IMD transceiver to switch power-consuming circuitry in the IMD to a sleep, power-down mode of operation for a predetermined sleep time period.

15 Claims, 2 Drawing Sheets

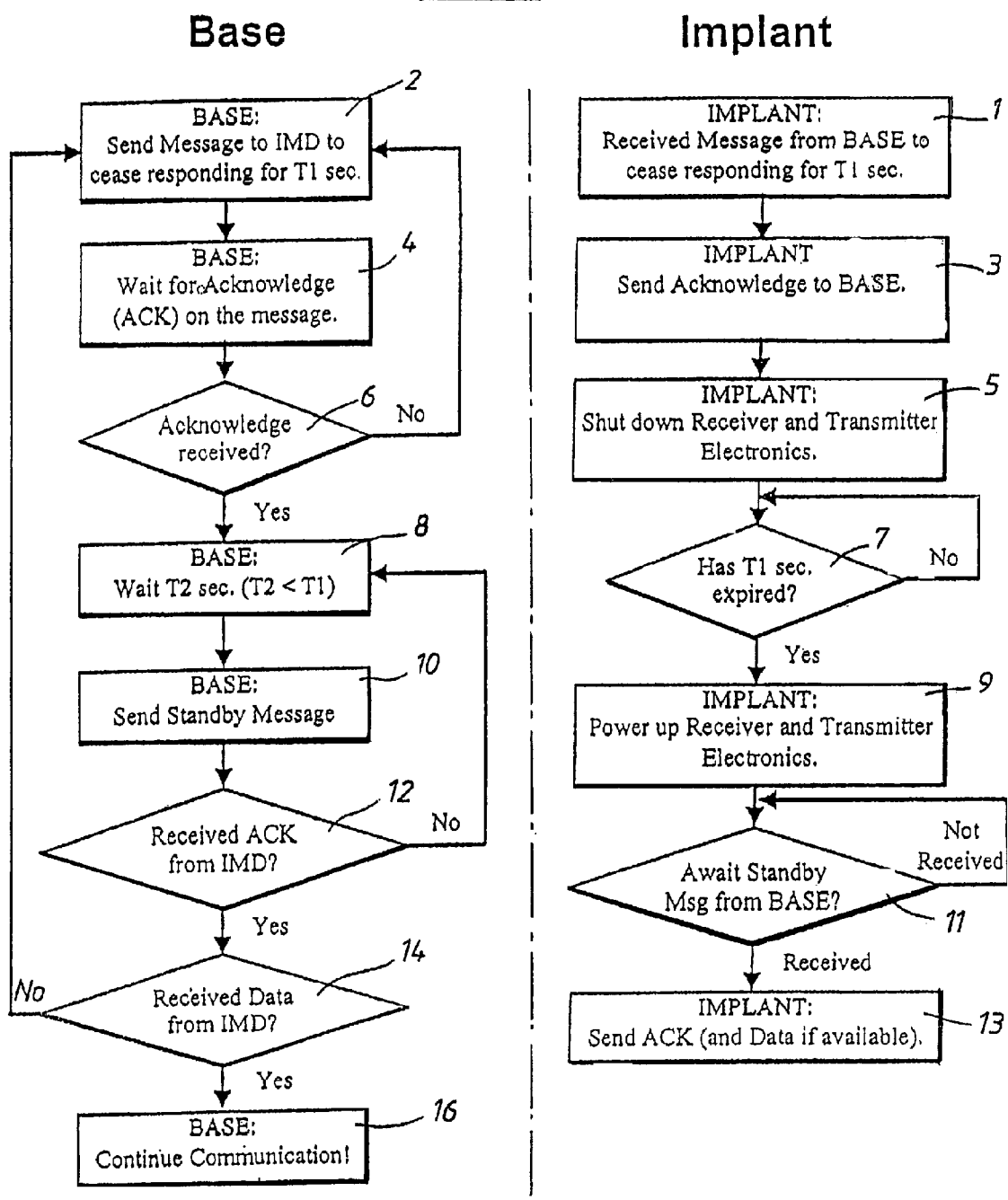

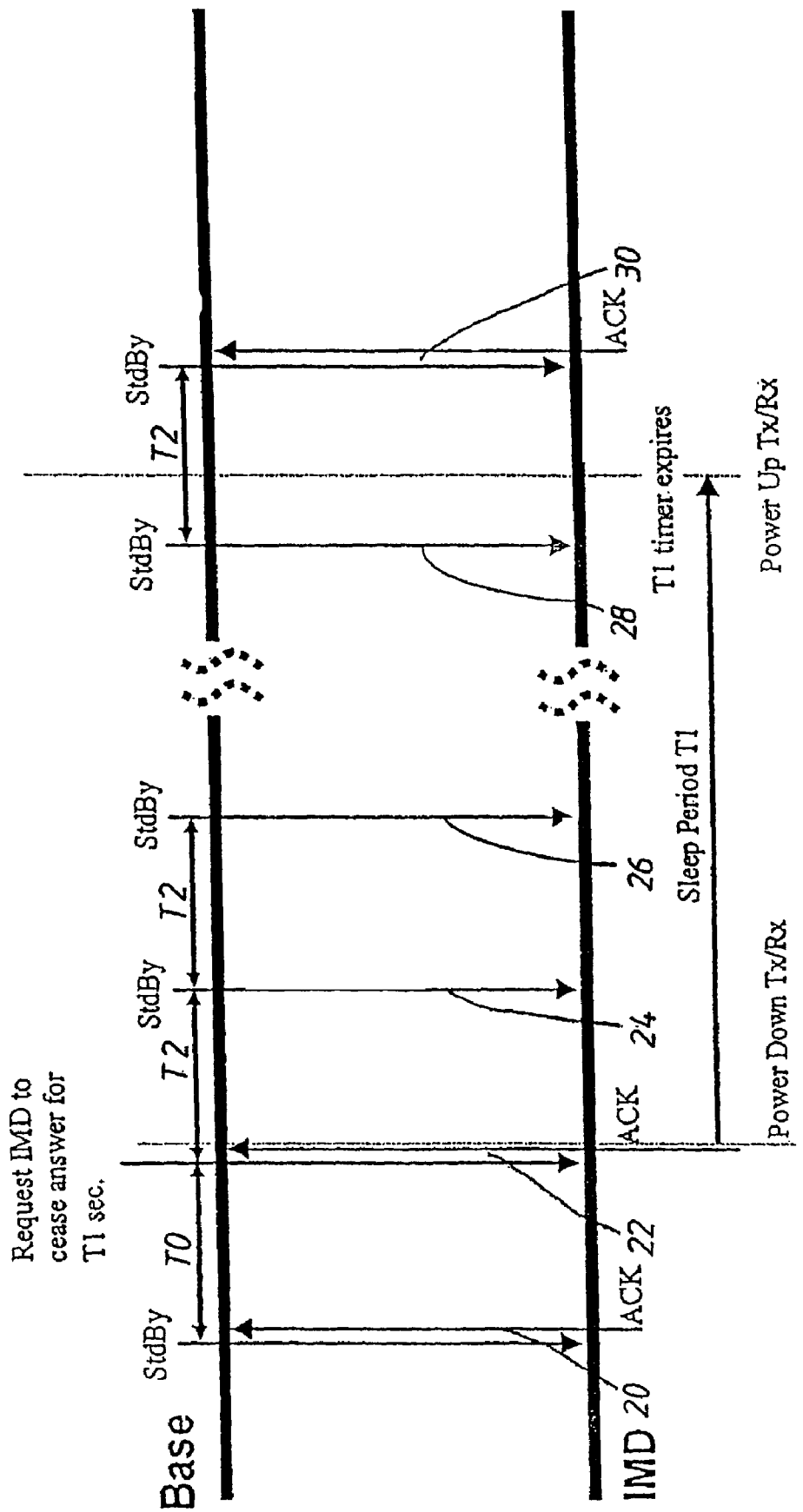

SYSTEM AND METHOD FOR RADIO COMMUNICATION BETWEEN AN IMPLANTABLE MEDICAL DEVICE AND AN EXTERNAL BASE UNIT

BACKGROUND OF THE INVENTION

1. Field of the Invention

The present invention relates to a system for radio communication between an implantable medical device, IMD, and an external base unit, the IMD having a transceiver for communication with the external base unit, as well as to a corresponding method of radio communication.

2. Description of the Prior Art

Systems for communication between an IMD and an external management device or base unit are well known, see e.g. U.S. Patent Application Publication No. 2004/0122488. In this way clinical and other data are retrieved from the IMD and the operation of the IMD is controlled from the outside of the patient.

In systems of this kind including an IMD communicating with an external base unit continuous efforts are made to save power in electrical IMDs to prolong the IMD battery life time.

SUMMARY OF THE INVENTION

An object of the present invention is to reduce the power consumption in the IMD for the radio communication with the external unit.

This object is achieved according to the invention by saving power by switching the IMD transceiver electronics to a sleep mode of operation for a predetermined sleep time period, in which the communication of information between external base unit and IMD is reduced. With the IMD in such a sleep mode it becomes very quickly operative at the expiration of the sleep time period.

Certain communication standards prescribe that a radio communication channel of an Medical Implant Communication Systems, MICS, is to be regarded as free to use if no communication activity is detected within a prescribed silent time period. To obtain a reliable system for communication between an IMD and an external base unit based on these standards messages must be sent from the base unit to the IMD sufficiently frequent to avoid loosing the right to the channel and sent messages must result in immediate responses from the IMD. However, to maintain the communication channel between the base unit and the IMD also during the sleep time period of the IMD transceiver, according to embodiments of the invention, the base unit is arranged to start sending, in absence of communication activity on the communication channel, a radio signal in the form of standby messages on the communication channel before the expire of said silent time period. The IMD is adapted to acknowledge to the base unit receipt of said sleep message but not acknowledge receipt of any messages received in the sleep mode of operation. Thus, in this way the communication channel is maintained in the absence of communication on the channel by the base unit sending standby messages with sufficiently high frequency without consuming current from the IMD battery for IMD acknowledgements of the standby messages.

According to another embodiment of the system according to the invention the standby messages contain empty data packets sent with intervals shorter than the silent time period.

BRIEF DESCRIPTION OF THE DRAWINGS

FIG. 1 is a flow chart illustrating the functioning of the base unit and the implant (IMD) in accordance with the present invention.

FIG. 2 is a time sequence diagram for assisting in the explanation of FIG. 1.

DESCRIPTION OF THE PREFERRED EMBODIMENTS

FIG. 1 shows flow charts illustrating the function of the base unit, Base, and the IMD, Implant, respectively of the present invention.

When it is suitable according to a predetermined criterion, e.g. when the flow of data on the communication channel between base unit and IMD is reduced, the base unit sends a sleep message to the IMD requesting the IMD transceiver to switch to a sleep power down mode for a predetermined sleep time period of length T1 in order to save power of the IMD battery. This sleep message instructs the IMD transceiver to cease responding to messages from the base unit for the time period T1. This is illustrated at step 2 in FIG. 1.

Receipt of this sleep message is illustrated at step 1 of the flow chart illustrating the function of the implant, IMD, and an acknowledgement of this sleep message is sent by the IMD, at step 3 in the implant flow chart. The base unit is waiting for this acknowledgement, at step 4 in FIG. 1, to know that this sleep message is received and understood.

If the base unit does not receive such an acknowledgement from the IMD, cf. step 6 in FIG. 1, another sleep message is sent by the base unit to the IMD.

Upon receipt of the sleep message the IMD transceiver electronics are shut down to a sleep mode of operation, at step 5 if the IMD flow chart, and a timer of the IMD is started to count the time period T1, cf. step 7 in the IMD flow chart.

According to the communications standards FCC MICS, Federal Communication Commission Medical Communication System/Service, and ETSI ULP-AMI, European Telecommunications Standards Institute Ultra Low Power—Active Medical Implant, a MICS radio communication channel is to be regarded as free to use if no activity is detected within a 10 msec period. To make telemetry system between an IMD and an external base unit reliable, messages sent from the base unit result in an immediate response from the IMD. This must occur at least once per 10 msec to secure that the right to the communication is not lost.

When the acknowledgement of the receipt of the sleep message is received by the base unit, at step 6 of the base unit flow chart in FIG. 1, the base unit starts sending, after a time interval T2 which is shorter than 10 msec, a radio signal on the communication channel in the form of standby messages or empty data packets just having a header. These standby messages or empty data packets are sent with the time interval T2 to comply with the mentioned MICS standard for maintaining the communication channel to the IMD, see steps 8 and 10 in the base unit flow chart. In this sleep mode of the IMD the base unit is prepared that the standby messages are not acknowledged by the IMD.

The IMD is in the power saving sleep mode for the time period T1, cf. step 7 in the IMD flow chart in FIG. 1. When the time period T1 has expired the IMD receiver and transmitter are powered up, in step 9 in the IMD flow chart. This powering up can be performed in two alternative ways.

According to a first alternative the IMD transmitter is powered up at the end of the time period T1 and sends an acknowledgement to the base unit. As a second alternative the IMD powers up its receiver at the end of time period T1 and waits for the next standby message or empty data packet from the base unit. When this next standby message or empty data packet is received by the IMD receiver, the IMD transmitter is powered up and an acknowledgement is sent to the base unit.

The acknowledgement from the IMD is received by the base unit, at step 12 of the base unit flow chart, together with possible data which can be appended to the acknowledgment, at step 14 in the base unit flow chart of FIG. 1.

After the power up of the IMD transceiver the IMD is waiting for the next standby message, step 11 in the IMD flow chart, from the base unit, and is sending an acknowledgment of receipt of this next message together with possible available data to the base unit, at step 13 in the IMD flow chart.

If the base unit receives data from the IMD the communication between base unit and IMD continues, at step 16 in the base unit flow chart. If no data are received by the base unit from the IMD, and no more data is expected, the above described procedure is started again by the base unit sending a sleep message to the IMD transceiver requesting the IMD transceiver to switch to the sleep mode for the time period T1.

The above described procedure starting by the base unit sending a sleep message to the IMD can also be restarted in response to other predetermined criteria.

FIG. 2 illustrates an example of a time sequence of messages or data packets exchanged between the base unit and the IMD in the procedure described above with reference to FIG. 1.

As appears from FIG. 2 the base unit is sending standby messages, StdBy in the figure, with an interval of T2 to the IMD, and the IMD is returning an acknowledgement, ACK, to the base unit, at 20 in FIG. 2. After a time TO after this acknowledgement 20 the base unit is sending a sleep message to the IMD, requesting the IMD to power down its transmitter Tx and receiver Rx to the sleep mode wherein answering of any messages from the base unit is stopped, at 22 in the figure. The base unit continues to send standby messages StdBy at 24, 26, . . . 28 to maintain the communication channel to the IMD as described above, but to save power no acknowledgments are sent by the IMD in the sleep time period T1. At the end of the sleep mode the IMD transceiver Tx/Rx is powered up, and the first standby message StdBy received thereafter is acknowledged, at 30 in FIG. 2. After possible data exchange between base unit and IMD, or in response to another predetermined criterion, this procedure is restarted.

As is apparent from the description above and FIG. 2 the time period T1 is longer than the time T2. According to the standards discussed above the time T2 must be less than 10 msec, whereas the time period T1 can typically be of the order of 0.05-1.0 sec.

In the embodiment described above it is assumed that the base unit initiates the data flow but, according to another embodiment of the invention, an equivalent data flow can be controlled by the IMD.

There are at least two ways to implement the basic data flow depending on the amount of hardware support available in the system according to the invention. These two ways can be characterized as software or hardware oriented embodiments of the invention. In a software oriented embodiment messages are sent between the application software in the base unit and the application software in the IMD. Each application performs actions necessary on their radio units to control sleep, wait and wakeup behaviour. In a hardware oriented embodiment of the invention one side, preferably the external base unit, can control the opposite side, IMD, by means of a special set of radio messages operating directly on the remote radio control unit to set timers and power down the radio transceiver.

Although modifications and changes may be suggested by those skilled in the art, it is the intention of the inventor to embody within the patent warranted heron all changes and modifications as reasonably and properly come within the scope of her contribution to the art.

I claim as my invention:

1. A system for radio communication between an implantable medical device and an external base unit comprising:
    a first transceiver in said implantable medical device;
    a second transceiver in said external base unit, said first and second transceivers communicating with each other via a communication channel;
    a message generator in said external base unit that, according to a predetermined criterion, generates a sleep message and causes said sleep message to be transmitted to said implantable medical device via said first and second transceivers;
    power-consuming circuitry in said implantable medical device that, upon receipt of said sleep message, automatically switched to a sleep power down operational mode for a predetermined sleep time;
    disconnect circuitry in at least one of said implantable medical device or said external base unit that disconnects said communication channel in an absence of communication activity in said communication channel during a silent time period of predetermined length;
    said message generator in said base unit generating at least one standby message and causing said standby message to be communicated via said communication channel before expiration of said silent time period, to maintain said communication channel open between said base unit and said implantable medical device; and
    an acknowledgment unit in said implantable medical device that acknowledges receipt of said sleep message to said base unit via said first and second transceivers, but does not acknowledge receipt of said standby message.

2. A system as claimed in claim 1 wherein said message generator generates said standby messages as empty data packets transmitted at intervals that are shorter than said silent time.

3. A system as claimed in claim 1 wherein said message generator generates and transmits said sleep message immediately after termination of transmission of an informational message to the implantable medical device or perception of an informational message from the implantable medical device.

4. A system as claimed in claim 1 wherein said circuitry in said implantable medical device comprises a timer that keeps the implantable medical device in said sleep mode for said predetermined sleep time period.

5. A system as claimed in claim 4 wherein said timer keeps said circuitry in said predetermined sleep time lasting between 0.5 and 1.0 seconds.

6. A system as claimed in claim 1 wherein said circuitry automatically supplies power to said second transceiver upon expiration of said predetermined sleep time period and transmits an acknowledgment to said external base unit.

7. A system as claimed in claim 1 wherein said second transceiver comprises a transmitter stage and receiver stage, and wherein said circuitry in said IMD supplies power to said receiver stage upon an expiration of said predetermined sleeping time and, in response to reception of a next standby message thereafter supplies power to said transmitter stage and causes transmission of an acknowledgement message to said external base unit.

8. A system as claimed in claim 1 wherein said first and second transceivers communicate according to the FCC MICS standard.

9. A system as claimed in claim 1 wherein said first and second transceivers communicate according to the ETS ULP-AM standard.

10. A system as claimed in claim 1 wherein said external base unit comprises a first telemetry circuit connected to said first transceiver and wherein said implantable medical device comprises a second telemetry circuit connected to said second transceiver.

11. A method for radio communication between an implantable medical device and an external base unit, each having a transceiver for communication therebetween, comprising the steps of:

at said external base unit, generating a sleep message according to a predetermined criterion and transmitting said sleep message from said external base unit to said implantable medical device;

upon receipt of said sleep message at said implantable medical device, automatically switching power-consuming circuitry in said implantable medical device to a power-down mode of operation for a predetermined sleep time period;

communicating between said implantable medical device and said external base unit via a communication channel, and disconnecting said communication channel if no communication activity is detected in the communication channel during a silent time period of a predetermined length;

before expiration of said silent time period, sending standby messages from said external base unit to said implantable medical device via said communication channel to maintain said communication channel active between said external base unit and said implantable medical device; and generating said standby messages as empty data packets and sending said empty data packets at intervals that are shorter than said silent time period.

12. A method as claim in claim 11 comprising sending said sleep message from said external base unit to the implantable medical device immediately after termination of transmitting information to, or receiving information from, the implantable medical device.

13. A method as claimed in claim 11 comprising acknowledging receipt of the sleep message by the implantable medical device by transmitting an acknowledgment message from the implantable medical device to the external base unit after receipt of the sleep message, and sending no acknowledgments by the implantable medical device while said implantable device is in said power-down mode.

14. A method as claimed in claim 11 comprising sending an acknowledgment message from the implantable medical device to the external base unit upon expiration of said sleep time period.

15. A method as claimed in claim 11 comprising, upon receipt of a first further message after expiration of said sleep time period, sending an acknowledgment message from the implantable medical device to the external base unit indicating receipt of said first further message.

* * * * *